United States Patent [19]

Künstle et al.

[11] 3,972,943

[45] Aug. 3, 1976

[54] PROCESS FOR PREPARING ALKALIACETYLACETONATES

[75] Inventors: Gerhard Künstle, Raitenhaslach; Herbert Siegl, Haiming, both of Germany

[73] Assignee: Wacker-Chemie GmbH, Munich, Germany

[22] Filed: Jan. 14, 1975

[21] Appl. No.: 540,782

[30] Foreign Application Priority Data

Jan. 18, 1974   Germany............................ 2402399

[52] U.S. Cl............................. 260/594; 260/632 A
[51] Int. Cl.² ....................................... C07C 45/00
[58] Field of Search....................... 260/594, 632 A

[56] References Cited
UNITED STATES PATENTS

| | | | |
|---|---|---|---|
| 2,760,987 | 8/1956 | Burness.............................. | 260/594 |
| 3,002,999 | 10/1961 | Lichtenberger et al. ............ | 260/594 |
| 3,497,558 | 2/1970 | Kohan et al. ...................... | 260/594 |

OTHER PUBLICATIONS

Terova et al., Russian Chemical Reviews, vol. 34, pp. 161–185 (1965).
Hatch et al., J. Org. Chem., vol. 13, pp. 249–253 (1948).

*Primary Examiner*—James O. Thomas, Jr.
*Assistant Examiner*—James H. Reamer
*Attorney, Agent, or Firm*—Allison C. Collard

[57]   ABSTRACT

A process for preparing alkaliacetylacetonates from acetylacetone and alkali hydroxide, which consists of slowly adding an aqueous alkali hydroxide solution to an at least stoichiometric amount of acetylacetone dissolved in acetone, while stirring; dissipating the generated reaction heat by cooling, separating the precipitated alkaliacetylacetonates formed in the reaction, rinsing with acetone, and drying. The products of the reaction may be used in a large number of addition and condensation reactions as one of the reagents, and are sometimes effective as catalysts.

5 Claims, No Drawings

PROCESS FOR PREPARING ALKALIACETYLACETONATES

The present invention relates to the preparation of alkaliacetylacetonates from acetylacetone and alkali hydroxide.

The following methods are described in the art for making alkaliacetylacetonates: By reacting acetylacetone with alkali hydroxides in aqueous or alcoholic media (Journal of Organic Chemistry, 13, 251, 1948); by direct reaction without solvent of the two reagents (Parson, "Zeitschrift fur anorganische Chemie", 40, 412, 1940); by reacting alkali carbonates or alcoholates with acetylacetone in alcohol or ether (Combes, Comptes rendues de l'Academie des Sciences, 105, 868, 1887); or by reacting the finely distributed metals with acetylacetone in toluene or ether (Combes, Annales de Chimie et de Physique, 6, 245, 1912).

The alkaliacetylacetonates obtained in comparatively low yields by these processes are of low purity throughout so that a recrystallization is necessary leading to further decrease in yields. Furthermore, the alkaliacetylacetonates usually have a very high water content and this promotes decomposition, which is ready to occur anyhow.

It is an object of the present invention to provide a process for preparing alkaliacetylacetonates, which in a single operation leads to high yields of the end product, that is, low in water content, and analytically pure.

A simple process has been found according to the invention for preparing alkaliacetylacetonates from acetylacetone and alkali hydroxide which consists in slowly adding an aqueous alkali hydroxide solution to an at least stoichiometric amount of acetylacetone dissolved in acetone, while stirring; dissipating the generated reaction heat by cooling, separating the alkaliacetylacetonates precipitated in the reaction, rinsing with acetone, and drying.

In carrying out the process, we proceed in general by adding slowly a preferably concentrated alkali hydroxide solution to a mixture of at least the stoichiometric amount of acetylacetone, preferably being in excess by 5–10 molar %, and the two-fold to four-fold amount by weight of acetone. The rate of addition is preferably so adjusted that the reaction temperature in the well-stirred and water cooled solution does not exceed 30°C. After addition of the alkali hydroxide solution, stirring is continued for some time, until the reaction has been completed, which can be observed by an even drop in temperature. The precipitated alkaliacetylacetonate is separated and washed with acetone. The reaction product, which is still moist from the acetone content, is then dried at a temperature of 20°–120°C, preferably at 60°–100°C, and at a reduced pressure of preferably 5-30 torr.

The products prepared according to the invention are obtained in finely crystallized form as colorless powders with a purity of more than 99%, and a water content below 0.8% by weight. They are used as enolates of acetylacetone, primarily as sodium and potassium acetylacetonate, in a large number of reactions of acetylacetone, particularly in condensations, e.g., with ethylene oxide to 3-hydroxiethylene-pentanedione –2.4. With primary chlorides RCl, wherein R represents, for example, benzyl, allyl, n-butyl, heptyl, octyl, they result in the respective substitution products. With esters of chlorocarbonic acid, they form mixed carbonates. They may add themselves to olefins under oxidation, e.g., to styrene with formation of 2.2-dimethoxi-5-phenyltetrahydrofurane-3-carboxylic acid methyl ester. As catalysts, they may be used, e.g., in the production of 2.6-dichlorophenols from cyclohexane and aldehydes.

EXAMPLE 1

Into a mixture of 2,000 ml acetone and 420 grams acetylacetone, 320 g. of sodium hydroxide solution (160 grams NaOH of 100% + 160 grams water) were added dropwise with cooling and stirring within one hour in such a manner that a reaction temperature of 25°C was not exceeded. The mushy reaction product was suctioned off at about 10°C and the solid was washed with a total amount of 300 ml acetone; this was followed by drying at 100°C and 10 torr.

Obtained were 481 grams sodium acetylacetonate, corresponding to 98.3% of the theoretical, calculated on the sodium hydroxide used at the start, the water content of the product being 0.27%. According to titration (with methyl orange), the filtrate contained further 2.64 grams $NaC_5H_7O_2$ or 0.55%.

| Analysis: | calculated | C 49.17 | H 5.74 | Na 18.85 |
|---|---|---|---|---|
| | found: | C 49.32 | H 5.90 | Na 18.65 |

EXAMPLE 2

Into a mixture of 3,000 ml acetone and 1,260 grams acetylacetone, a total amount of 1,346 grams potassium hydroxide (781 grams KOH of 85% + 565 grams water) were added dropwise within three hours, while stirring and cooling in such a manner that a reaction temperature of 25°C was not exceeded. After another hour of stirring, filtering with suction was applied and the solid was washed on the suction filter with 500 ml acetone. The reaction product, still moist from the acetone content, was dried at 100°C/10 torr.

Obtained were 1,626 grams potassium acetylacetonate, corresponding to 98.6% of the theoretical, calculated on the potassium hydroxide used at the start, the water content of the product being 0.8%.

| Analysis: | calculated | C 42.78 | H 5.50 | K 27.85 |
|---|---|---|---|---|
| | found | C 42.64 | H 5.41 | K 27.67 |

The above examples are given by way of illustration and not of limitations. Many variations in the details may be made without departing from the spirit of the invention.

What is claimed is:

1. A process for preparing alkaliacetylacetonates selected from the group consisting of potassium and sodium acetylacetonate, from acetylacetone and the respective alkali hydroxide, which consists of slowly adding, while stirring, a substantially saturated aqueous solution of said alkali hydroxide to a solution of acetylacetone in acetone, wherein acetylacetone is present from at least stoichiometric amount to 10 mol% of excess calculated on the amount of alkali hydroxide, the rate of addition of said alkali hydroxide solution being so adjusted that the reaction temperature does not exceed 30°C, dissipating the generated reaction heat by cooling, separating the precipitated alkaliacetylacetonate formed in the reaction, rinsing with acetone, and drying.

2. The process according to claim 1 wherein acetylacetone is used dissolved in the two to four-fold amount of acetone.

3. The process according to claim 1, wherein acetylacetone is used in an excess amount of from 5–10 molar per cent.

4. The process according to claim 1, wherein the separated alkaliacetylacetonate is dried at a temperature of 20°–120°C and a reduced pressure of 5–30 torr.

5. The process according to claim 4, wherein the separated alkaliacetylacetonate is dried at a temperature between 60 and 100°C and a pressure of 10 torr.

\* \* \* \* \*